(12) United States Patent
Teague et al.

(10) Patent No.: US 11,961,597 B1
(45) Date of Patent: *Apr. 16, 2024

(54) USER INTERFACE DETAIL OPTIMIZER

(71) Applicant: ALLSCRIPTS SOFTWARE, LLC, Chicago, IL (US)

(72) Inventors: Ross Carlyle Teague, Cary, NC (US); Mary Johnson, Raleigh, NC (US)

(73) Assignee: Allscripts Software, LLC, Chicago, IL (US)

( * ) Notice: Subject to any disclaimer, the term of this patent is extended or adjusted under 35 U.S.C. 154(b) by 748 days.

This patent is subject to a terminal disclaimer.

(21) Appl. No.: 16/414,340

(22) Filed: May 16, 2019

Related U.S. Application Data

(63) Continuation of application No. 14/292,909, filed on May 31, 2014, now Pat. No. 10,297,345.

(51) Int. Cl.
 *G16H 10/60* (2018.01)

(52) U.S. Cl.
 CPC .................... *G16H 10/60* (2018.01)

(58) Field of Classification Search
 CPC ...................................... G16H 10/60
 See application file for complete search history.

(56) References Cited

U.S. PATENT DOCUMENTS

| | | | | |
|---|---|---|---|---|
| 9,053,583 | B1 * | 6/2015 | Gross | G16H 15/00 |
| 2001/0008404 | A1 | 7/2001 | Naito et al. | |
| 2005/0063670 | A1 * | 3/2005 | Arai | H04N 5/76 |
| | | | | 386/241 |
| 2006/0080140 | A1 * | 4/2006 | Buttner | G16H 10/60 |
| | | | | 705/2 |
| 2010/0063840 | A1 * | 3/2010 | Hoyme | G16H 10/60 |
| | | | | 705/3 |
| 2010/0076786 | A1 | 3/2010 | Dalton et al. | |
| 2011/0054944 | A1 * | 3/2011 | Sandberg | G06Q 30/04 |
| | | | | 705/3 |
| 2011/0166880 | A1 * | 7/2011 | Keynan | G16H 10/60 |
| | | | | 705/2 |
| 2011/0201900 | A1 * | 8/2011 | Zhang | G16H 15/00 |
| | | | | 600/300 |
| 2012/0078647 | A1 * | 3/2012 | Grassle | G16H 40/67 |
| | | | | 705/2 |
| 2012/0310059 | A1 * | 12/2012 | Pinto | G16H 40/67 |
| | | | | 600/323 |
| 2014/0092095 | A1 * | 4/2014 | Higgins | G06F 3/0481 |
| | | | | 345/440 |
| 2016/0070683 | A1 * | 3/2016 | Thörn | H04W 4/029 |
| | | | | 715/229 |

* cited by examiner

*Primary Examiner* — Peter H Choi
*Assistant Examiner* — Aaisha Abdullah
(74) *Attorney, Agent, or Firm* — Peter Zura; LOZA & LOZA, LLP

(57) ABSTRACT

Technologies and techniques for optimizing a patient overview in a user interface (UI), utilizing at least one processor. An optimize request is received including an optimization level from a user via the UI, selecting predetermined patient information associated with the received optimization level, and displaying an optimized patient overview containing the selected certain patient information to the user.

14 Claims, 5 Drawing Sheets

LOPEZ, Alexander (Alex)

Age:
75 years

Address:
918 Cove Dr.
Richmond, VA

Phone:
612-356-7831

Insurance:
BCBS

Conditions

| | |
|---|---|
| Heart failure | 5/7/2014 |
| Diabetes | 10/16/1997 |
| Hypertension | 9/22/1996 |

Family History

| | | |
|---|---|---|
| Brother | Deceased | Arthritis |
| Father | Deceased | Diabetes |
| Mother | | Glaucoma |

Allergies

| Description | Reaction |
|---|---|
| Latex | Hives |
| Peanuts | Hives |
| Pet dander | Hives |

Vitals

| | |
|---|---|
| Height | 67 inches |
| Weight | 175 LBS |
| BP | 130/90 |

Encounters — 210

5/9/2014 — Jenkins Family...
5/7/2014 — Lincoln ED
3/10/2014 — Jenkins Family...
12/9/2013 — Jenkins Family...
4/10/2013 — Telephone
1/9/2013 — Jenkins Family...
10/7/2012 — Lincoln ED
5/10/2012 — Liberty Hospital
8/9/2011 — Jenkins Family...
5/7/2011 — Lincoln ED 5/10/2014 — Liberty Hospital CC: Fever and vomiting. Pt: 1 day ago pt complained of high fever (102.8). Nausea and vomiting symptoms have increased.

ROS:
CHEST:
- tightness
RESP:

[5 seconds] — 220
[15 seconds] — 222
[FullView] — 224

USER INTERFACE DETAIL OPTIMIZER

CROSS-REFERENCE TO RELATED APPLICATION

The present application is a U.S. continuation patent application of, and claims priority under 35 U.S.C. § 120 to, U.S. non-provisional patent application Ser. No. 14/292,909, titled "USER INTERFACE DETAIL OPTIMIZER" to Teague et al., filed May 31, 2014, which is incorporated by reference in its entirety herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention relates to computing devices. More specifically, the present invention relates to displaying content on a computing device.

Often in acute settings providers are challenged to make quick decisions on patient care. When examining a patient, the provider has access to a patient overview to review the patient's patient information. Typically, on the patient overview, there is either too much, or too little, information displayed to the provider. Depending on the amount of time or other factors, the provider may want to see more or less information in patient overview.

Currently, there is no way for the provider to adjust the information that is displayed. Therefore, there exists a need for an improved method and system for displaying information in a user interface. This and other needs are addressed by one or more aspects of the present invention.

SUMMARY OF THE INVENTION

The present invention includes many aspects and features. Moreover, while many aspects and features relate to, and are described in, the context of healthcare applications, the present invention is not limited to use only in this context, as will become apparent from the following summaries and detailed descriptions of aspects, features, and one or more embodiments of the present invention.

Accordingly, one aspect of the present invention relates to a non-transitory computer readable medium storing a computer program for optimizing a patient overview in a user interface (UI), the computer program executable by at least one processor. The computer program comprising a set of instructions for receiving an optimize request including an optimization level from a user via the UI, selecting predetermined patient information associated with the received optimization level, and displaying an optimized patient overview containing the selected certain patient information to the user.

In a feature of this aspect, the optimization level is an amount of time available for the user to review the patient overview.

In another feature of this aspect, the amount of time available is one of 10 seconds, 30 seconds, 1 minute and 5 minutes, wherein the longer the user has to view the information, the more detailed patient information is displayed.

In another feature of this aspect, the optimization level is an amount of information desired to me viewed by the user.

In another feature of this aspect, the optimization level is selected from one of small, medium, large and complete, wherein the more information desired to be viewed by the user, the more detailed patient information is displayed.

In another feature of this aspect, the predetermined patient information is set by the user.

In another feature of this aspect, an initial view of the patient overview is a preset preference.

Another aspect of the present invention relates to a computing device comprising: one or more processors, and a non-transitory computer readable medium storing a computer program for optimizing a patient overview in a user interface (UI), the computer program executable by at least one of the one or more processors. The computer program comprising a set of instructions for receiving an optimize request including an optimization level from a user via the UI, selecting predetermined patient information associated with the received optimization level, and displaying an optimized patient overview containing the selected certain patient information to the user.

In a feature of this aspect, the optimization level is an amount of time available for the user to review the patient overview.

In another feature of this aspect, the amount of time available is one of 10 seconds, 30 seconds, 1 minute and 5 minutes, wherein the longer the user has to view the information, the more detailed patient information is displayed.

In another feature of this aspect, the optimization level is an amount of information desired to me viewed by the user.

In another feature of this aspect, the optimization level is selected from one of small, medium, large and complete, wherein the more information desired to be viewed by the user, the more detailed patient information is displayed.

In another feature of this aspect, the predetermined patient information is set by the user.

In another feature of this aspect, an initial view of the patient overview is a preset preference.

In addition to the aforementioned aspects and features of the present invention, it should be noted that the present invention further encompasses the various possible combinations and sub combinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIG. 2 is an example illustration of a user interface including a patient overview optimized to full in accordance with a disclosed implementation of the present invention;

FIG. 3 is an example illustration of a the user interface including a patient overview optimized for a 5 second view in accordance with a disclosed implementation of the present invention;

DETAILED DESCRIPTION

Figure 1:
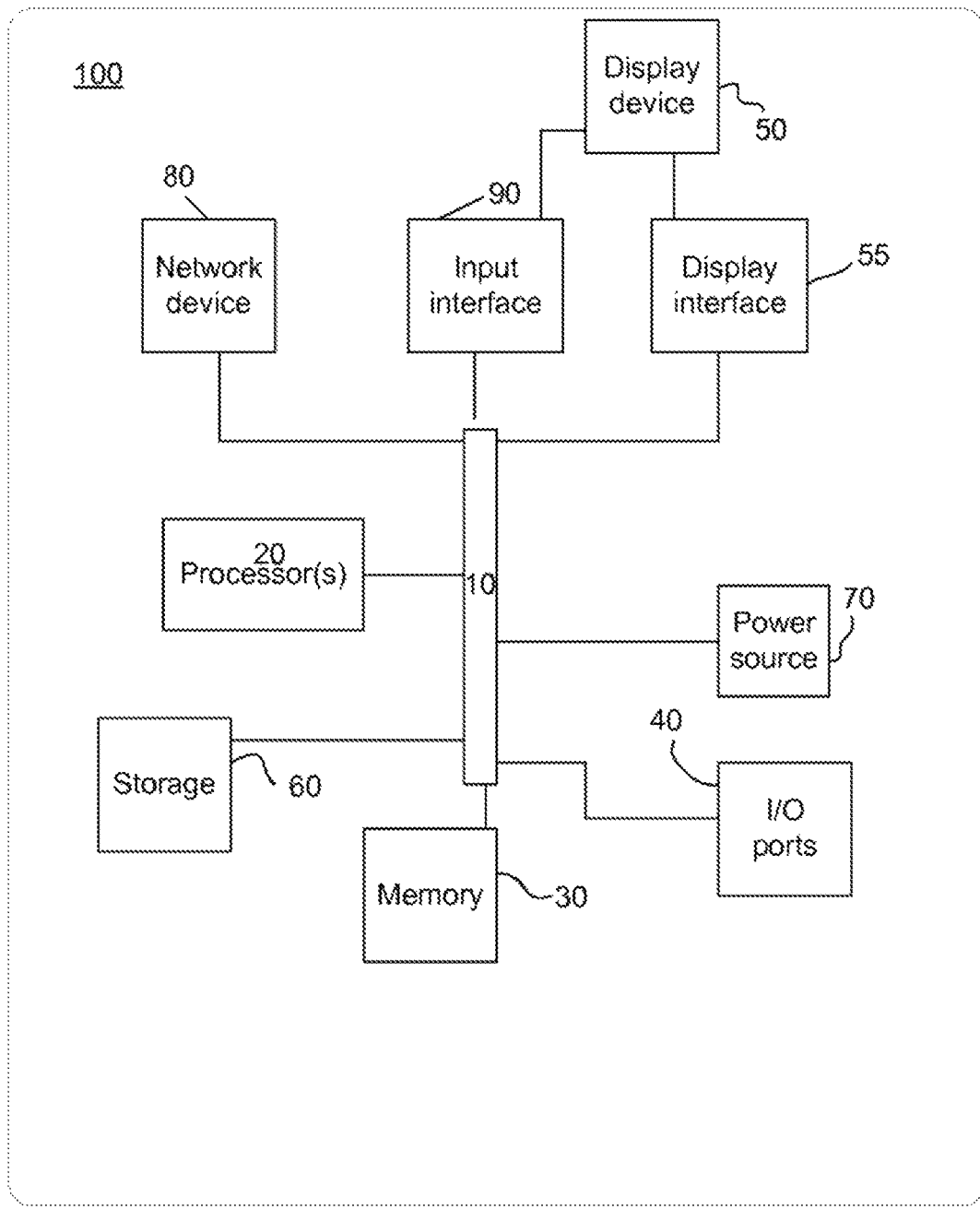
FIG. 1 is an example illustration of a computing device in accordance with a disclosed implementation of the present invention.

Referring now to the drawings, one or more preferred embodiments of the present invention are next described. The following description of one or more preferred embodiments is merely exemplary in nature and is in no way intended to limit the invention, its implementations, or uses.

As a preliminary matter, it will readily be understood by one having ordinary skill in the relevant art ("Ordinary Artisan") that the present invention has broad utility and application. As should be understood, any embodiment may incorporate only one or a plurality of the above disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein-as understood by the Ordinary Artisan based on the contextual use of such term-differs in any way from any particular dictionary definition of such term, it is intended that the meaning of the term as understood by the Ordinary Artisan should prevail.

Systems, methods, and computer-readable media for adjusting the display of content on a computing device based on the user's gaze. When the user interface displayed on a mobile device is adjusted because the user changes the orientation of the device, an optimum orientation of the user interface is determined based on the user's gaze. If the orientation of the UI is not the same as the optimal orientation, the orientation of the contents of the UI is adjusted to the optimal orientation.

A method and system are disclosed that filters patient data and only highlights the relevant, most impactful data that could improve provider response times and reduce oversights. The system and method allows a user/provider that optimizes the amount of information presented in a user interface (UI) based on the amount of time that the provider has to prepare for a patient session.

An example of a suitable computing device operable in accordance with an implementation of the disclosed system and method set forth below is illustrated in FIG. 1. It should be noted that the various functional blocks shown in FIG. 1 may include hardware elements, software elements (including computer code or instructions stored on a non-transitory machine-readable medium) or a combination of both hardware and software elements. The computing device 100 may be implemented in different forms. For example, the computing device 100 may be implemented as a server, group of servers, a desktop computer, laptop, workstation, personal digital assistant (PDA) and other appropriate computers. The computing device 100 includes a bus 10, display interface 55, display device 50, I/O ports 40, input interface 90, data processing circuitry, such as one or more processors 20, a memory device 30, a non-volatile storage 60, a networking device 80 and a power source 70.

The computing device may be implemented as a mobile computing device. The mobile computing device may be implemented by various mobile devices, such as PDAs, cellular phones, smart phones, tablets and other similar computing devices. The mobile computing device includes a bus, a display, I/O ports, Input displays, one or more processors, a memory device, a non-volatile storage, a networking device, a power source, similar to the computing device 100 illustrated in FIG. 1. The mobile computing device further includes a transceiver for implementing wireless communication under various protocols, such as SMS or MMS messaging, CDMA, TDMA, WCDMA or GPRS, among others. The components of the computing devices as shown, their connections and relationships and their functions are meant for exemplary purposes only, and are not meant to limit implementations of the disclosed inventions described and/or claimed in this disclosure.

The display device 50 may be used to display images generated by the computing device 100, for example a graphical user interface (GUI). The display 50 may be any type of display such as a cathode ray tube (CRT), a liquid crystal display (LCD), a light emitting diode (LED) display, or other suitable display. In certain implementations of the computing device 100, the display 50 may include a touch-sensitive element, such as a touch screen.

The processor(s) 20 may provide data processing capability to execute and support one or more operating systems, computer programs, user and application interfaces, software systems and applications, and any other functions of the computing device 100 that may be stored in a memory on the processor 20, the memory device 30 or on the storage device 60. The processor(s) 20 may include one or more microprocessors, such as one or more "general purpose" microprocessors, one or more special-purpose microprocessors and/or ASICS, for example.

The processor(s) 20 may communicate with a user through input interface 90 and display interface 55 coupled to the display 50. The display interface 55 may comprise appropriate circuitry for driving the display 50 to present graphical and other information to a user. The input interface 90 may receive commands from a user and convert them for submission to the processor 20.

The instructions or data to be processed by the processor(s) 20 may be stored in a memory 30. The memory 30 may be provided as a volatile memory, such as random access memory (RAM), and/or as a non-volatile memory, such as read-only memory (ROM). The memory 30 may store a variety of information and may be used for various purposes. For example, the memory 30 may store firmware executed by a processor 20 (such as a method for modifying the orientation of the contents displayed in a user interface on a computing device as discussed herein), other programs that enable various functions of the computing device 100, user interface functions, and processor functions. The memory 30 may also be another form of computer-readable medium.

The components may further include a non-volatile storage 60 for persistent storage of data and/or instructions. The non-volatile storage 60 may include flash memory, a hard drive, or any other optical, magnetic, and/or solid-state storage media. The non-volatile storage 60 may be used to store data files, software, wireless connection information (e.g., information that may enable the computing device 100 to establish a wireless connection, and any other suitable data. In addition, the non-volatile storage 60 may also store code and/or data for implementing various functions of the computing device 100, such as application or program code, data associated with such applications or programs, operating system code, user configured preferences, as well as code for implementing a method for modifying the orientation of the contents displayed in a user interface on a computing device as discussed herein. In implementation, the storage device 60 may be or contain a computer-readable medium.

A computer program product can be tangibly embodied in an information carrier. The computer program products may also contain instructions that, when executed, perform one or more methods, such as those described below. The information carrier is a computer- or machine-readable medium, such as the memory 30, the storage device 60, memory on processor 20, or a propagated signal.

A machine-readable medium includes any mechanism for storing or transmitting information in a form readable by a machine (e.g., a computer). For example, a machine readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

The disclosed system and methods are preferably implemented by software, hardware, or a combination of hardware and software. The disclosed implementations can include implementation in one or more computer programs that are executable and/or interpretable on a programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in an appropriate programming language. As used herein, the terms "machine-readable medium" "computer-readable medium" refers to any computer program product, apparatus and/or device (e.g., magnetic discs, optical disks, memory) used to provide machine instruction and/or data to a programmable processor. The computer readable medium can also be distributed over network coupled computer systems so that the computer readable code is stored and executed in a distributed fashion.

An implementation of a system and method for optimizing a user interface (UI) displayed to a user on a computing device. A user interface (UI) presented to a user may display a detailed report including a large amount of information. In the disclosed implementation a patient overview is the detailed report used as an example presented to a user in the UI over the display 50. Although this disclosure relates to a healthcare patient overview, any information that is presented to a user may be used with the disclosed system and method.

When a provider selects to view a patient's patient overview, the user is presented an option to optimize the information that is presented in the patient overview. The option may be a zoom button, a slider, or one or more buttons that indicate a certain optimized level. An example illustration of a user interface including a patient overview including a plurality of optimize buttons is shown in FIG. 2. As illustrated, the user interface 200 includes a detailed patient overview 210 and a plurality of optimize buttons 220, 222, 224. The plurality of optimize buttons 220, 222, 224 allows the user to select the amount of patient information that is displayed to the user in the patient overview. In the example illustrated in FIG. 2, the user may request that the patient overview be optimized based on the amount of time the user has to view the patient overview. In accordance with this implementation, the longer the user has to view the information, the more information is presented to the user. Conversely, the lesser amount of time that the user has to view the patient overview, the less information is displayed to the user.

In accordance with the disclosed implementation, three optimizing buttons are included in the UI to allow the user to select the level of optimization. As illustrated in FIG. 2, optimize button 220, labeled 5 secs, indicates that the user has only 5 seconds to review the information in the patient overview 210. In accordance with the disclosed system and method, the least amount of information in the patient overview is shown to the user. Optimize button 222, labeled 15 secs, indicates that the user has 15 seconds to review the information, and therefore, when selected displays more information in the patient overview than the optimize button 220. The optimize button 224, labeled Full, indicates that the user has enough time to review all of the information in the patient overview.

As indicated above, the optimize buttons may be in the form of a continuous control (e.g., a slider, radio dial) or drop down menu that includes the different optimization levels.

In an alternative implementation, how information is shown may also be related to how much time is selected for viewing the information to allow the user to learn more in a shorter amount of time. For example, when the 5 second optimize button 220 is selected, the user that this option of seeing a visual representation of the information (i.e., graphical), whereas if a 1 minute optimize button is selected, the user may see the detailed numbers shown in the visual representation.

Figure 5:
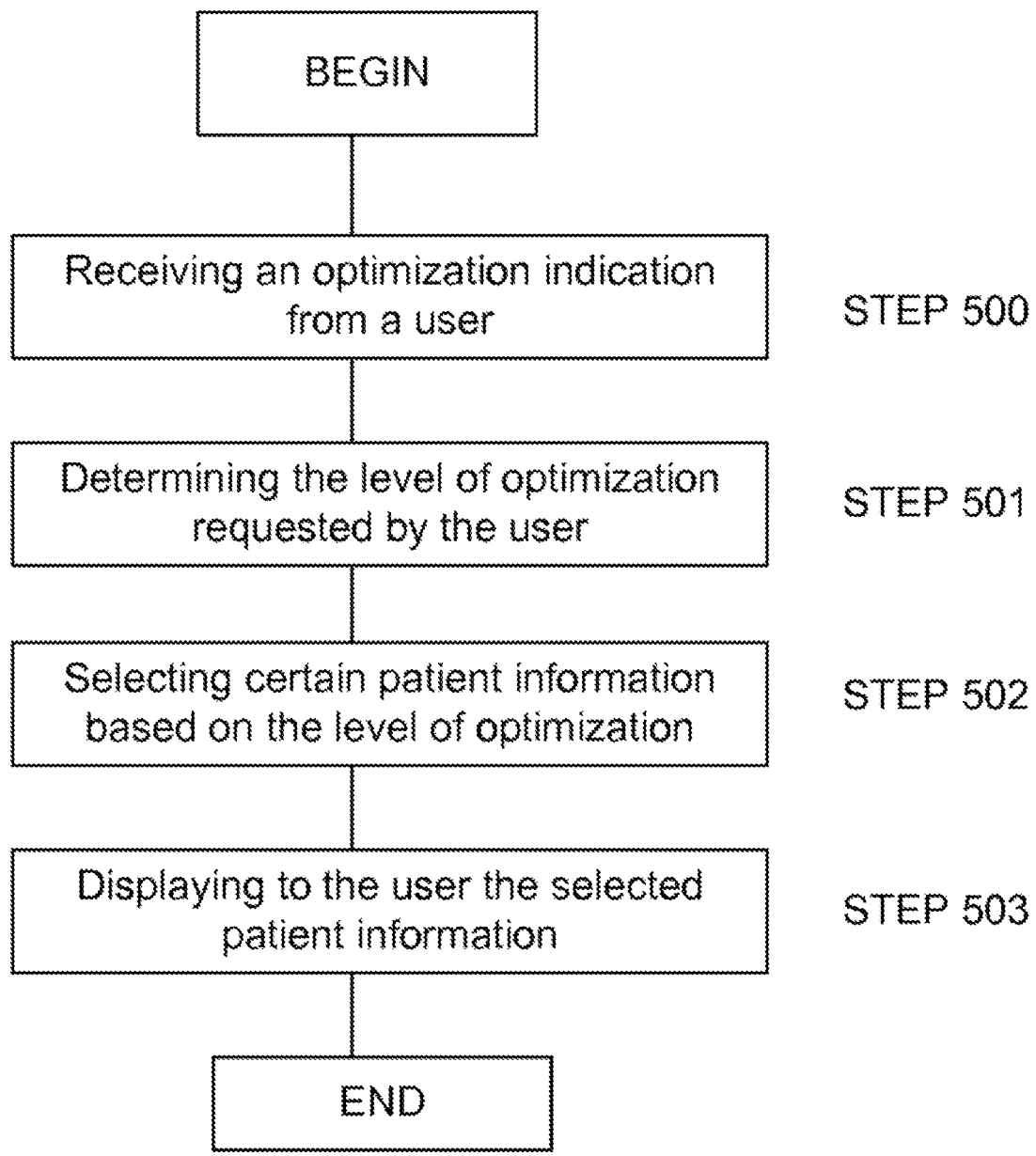
FIG. 5 is an example flow diagram of the method in accordance with a disclosed implementation of the present invention.

An example flow diagram of an implementation of the disclosed method is illustrated in FIG. 5. An optimizer processor 20, illustrated in FIG. 1, receives an indication from the user via the user interface to optimize the patient overview. STEP 500. When the optimizer processor 20 receives the optimize indication, the optimizer processor 20 determines the optimization level selected by the user, STEP 501, and selects certain predetermined information from the patient overview to display to the user. STEP 502. The predetermined information (i.e., content) that is selected for each optimization level may be preset by the user, other administrator, or by the program administrator. It is preferable that the predetermined information be able to be modified by the user and saved for future optimization by the user.

In an alternative implementation, a different predetermined information set may be saved for each of a plurality of users, such that the predetermined information that is selected for each optimization level is dependent on the user requesting the patient overview.

In accordance with a preferred implementation, the first view of the patient overview is a preset preference. Accordingly, the initial view of the patient overview may be any optimization level preselected by the user. In the disclosed implementation illustrated in FIG. 2, a full view of the patient overview is displayed to the user when the user selects to view the patient overview.

Once the optimizer processor 20 selects the appropriate predetermined information, the optimizer processor 20 forwards the selected predetermined information to the user interface for display to the user. STEP 503.

Figure 3:
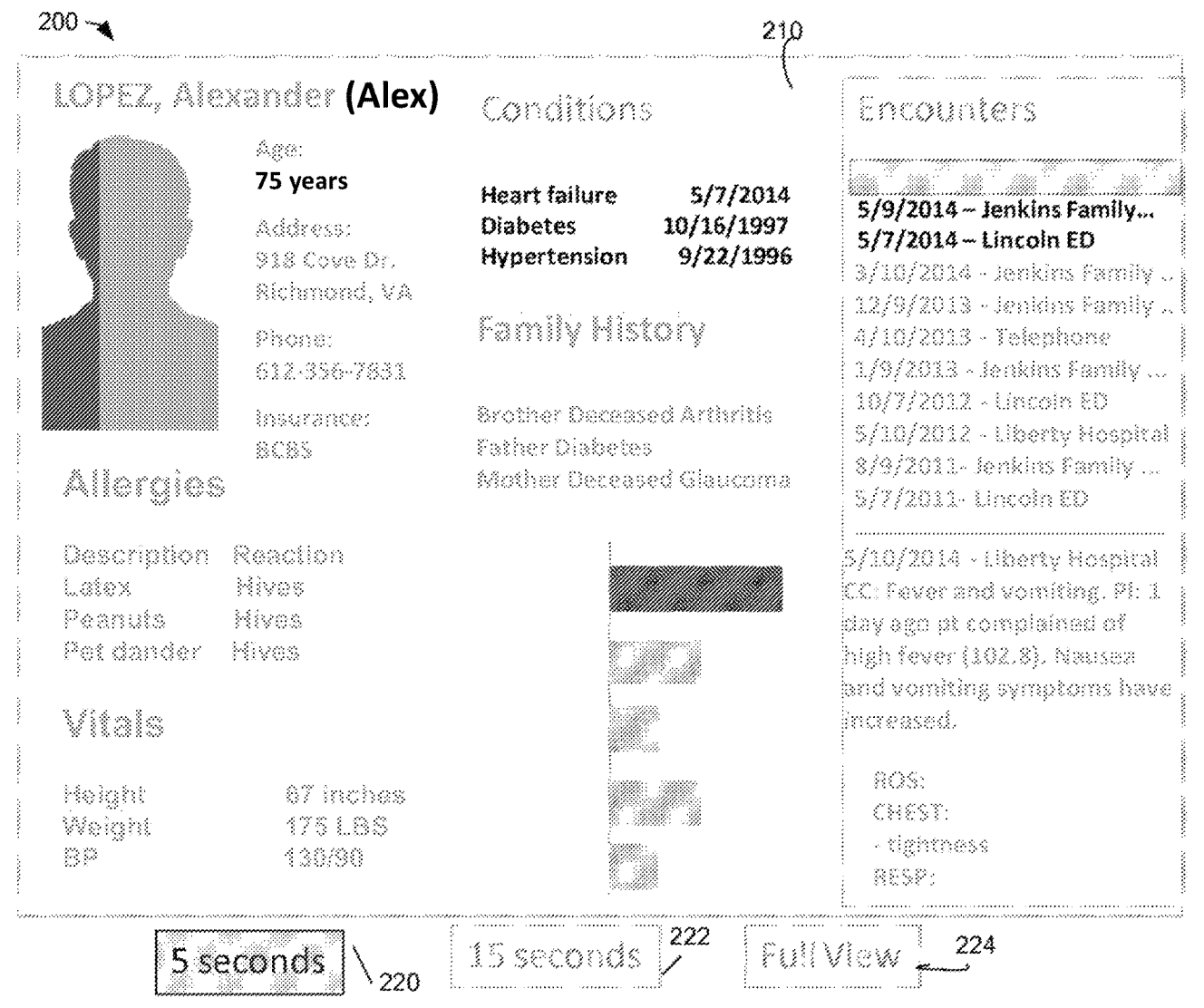

An example illustration of the optimized patient overview when the user has selected the 5 sec. optimize button 220 is shown in FIG. 3. As shown, the user has selected optimize button 220. Once the optimizer processor receives the optimize indication and determines the optimization level, the optimizer processor retrieves the appropriate predetermined patient information and displays the patient overview using only the selected predetermined patient information.

Figure 4:
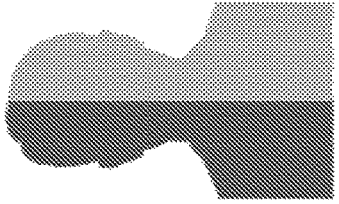
FIG. 4 is an example illustration of a the user interface including a patient overview optimized for a 15 second view in accordance with a disclosed implementation of the present invention.

An example illustration of the optimized patient overview when the user has selected the 15 sec. optimize button 222 is shown in FIG. 4. As shown, the user has selected optimize button 222. Once the optimizer processor receives the optimize indication and determines the optimization level, the optimizer processor retrieves the appropriate predetermined patient information and displays the patient overview using only the selected predetermined patient information.

The disclosed system and method for optimizing the user interface goes beyond a user "configuring their own home page" by selecting the content to be displayed. It allows a user to set what content is displayed, the amount that is displayed, and to quickly shift between those settings at the user's point of need.

In accordance with this disclosure, optimized information can be tied to events (e.g., a patient reason for visit), what is happening on the clinicians calendar (e.g., multiple patients waiting to be seen), time of day, etc.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A processor-based method for optimizing data generated in a medical processing device for a predetermined time period, comprising:
   generating, via a processing circuit of the medical processing device, a graphical user interface (GUI) comprising one or more user interface elements, wherein the graphical user interface comprises a patient overview including a plurality of patient data elements arranged in a first configuration;
   receiving a first input, via the user interface elements, comprising a first optimize request for the patient overview to be optimized to a first optimization level based on a first indicated amount of time the user has for review of the patient overview; and
   updating, via the processing circuit, the GUI to generate a first optimized patient overview based on the first optimize request, wherein the first optimized patient overview is based on a first predetermined patient information for use in the medical processing device that is associated with the first optimization level, and wherein the first optimized patient overview
   (i) displays only the patient data elements of the plurality of patient data elements that correspond to the first predetermined patient information for the first patient,
   (ii) displays, for the first patient data element, a graphical representation of a first vital measurement for the first patient in lieu of a previously displayed numerical value for the first vital measurement,
   (iii) wherein at least some patient data elements of the full patient overview are not displayed in the first optimized patient overview, and wherein the displayed patient data elements of the first optimized patient overview are still arranged in the first configuration.

2. The processor-based method of claim 1, further comprising:
   receiving a second input, via the user interface elements, comprising a second optimize request for the patient overview to be optimized to a second optimization level based on a second indicated amount of time the user has for review of the patient overview;
   updating, via the processing circuit, the GUI to generate a second optimized patient overview based on the second optimize request, wherein the second optimized patient overview is based on a second predetermined patient information for use in the medical processing device that is associated with the second optimization level.

3. The processor-based method of claim 2, wherein the second optimized patient overview (i) displays only the patient data elements of the plurality of patient data elements that correspond to the selected second predetermined patient information for the first patient, and (ii) displays, for the first patient data element, a numerical value for the first vital measurement, (iii) wherein at least some patient data elements that were displayed in the full patient overview are not displayed in the second optimized patient overview, (iv) wherein at least some patient data elements displayed in the second optimized patient overview were not displayed in the first optimized patient overview, and (v) wherein the displayed patient data elements of the second optimized patient overview are still arranged in the first configuration.

4. The processor-based method of claim 1, wherein at least one of the user interface elements comprises a slider.

5. The processor-based method of claim 1, wherein at least one of the user interface elements comprises a button.

6. The processor-based method of claim 2, wherein at least one of the first indicated amount of time and the second indicated amount of time comprises a value of thirty seconds or less.

7. The processor-based method of claim 2, wherein at least one of the first indicated amount of time and the second indicated amount of time comprises a value of thirty seconds or more.

8. A medical processing device configured to optimize data generated for a predetermined time period, comprising:
a display; and
a processing circuit operatively coupled to the display, wherein the processing circuit is configured to
generate a graphical user interface (GUI) comprising one or more user interface elements, wherein the graphical user interface comprises a patient overview including a plurality of patient data elements arranged in a first configuration;
receive a first input, via the user interface elements, comprising a first optimize request for the patient overview to be optimized to a first optimization level based on a first indicated amount of time the user has for review of the patient overview;
update the GUI to generate a first optimized patient overview based on the first optimize request, wherein the first optimized patient overview is based on a first predetermined patient information for use in the medical processing device that is associated with the first optimization level, and wherein the first optimized patient overview;
(i) displays only the patient data elements of the plurality of patient data elements that correspond to the first predetermined patient information for the first patient, (ii) displays, for the first patient data element, a graphical representation of a first vital measurement for the first patient in lieu of a previously displayed numerical value for the first vital measurement, (iii) wherein at least some patient data elements of the full patient overview are not displayed in the first optimized patient overview, and wherein the displayed patient data elements of the first optimized patient overview are still arranged in the first configuration.

9. The medical processing device of claim 8, wherein the processing circuit is further configured to:
receive a second input, via the user interface elements, comprising a second optimize request for the patient overview to be optimized to a second optimization level based on a second indicated amount of time the user has for review of the patient overview;
update the GUI to generate a second optimized patient overview based on the second optimize request, wherein the second optimized patient overview is based on a second predetermined patient information for use in the medical processing device that is associated with the second optimization level.

10. The medical processing device of claim 9, wherein the second optimized patient overview
(i) displays only the patient data elements of the plurality of patient data elements that correspond to the selected second predetermined patient information for the first patient, and (ii) displays, for the first patient data element, a numerical value for the first vital measurement, (iii) wherein at least some patient data elements that were displayed in the full patient overview are not displayed in the second optimized patient overview, (iv) wherein at least some patient data elements displayed in the second optimized patient overview were not displayed in the first optimized patient overview, and (v) wherein the displayed patient data elements of the second optimized patient overview are still arranged in the first configuration.

11. The medical processing device of claim 8, wherein at least one of the user interface elements comprises a slider.

12. The medical processing device of claim 8, wherein at least one of the user interface elements comprises a button.

13. The medical processing device of claim 9, wherein at least one of the first indicated amount of time and the second indicated amount of time comprises a value of thirty seconds or less.

14. The medical processing device of claim 9, wherein at least one of the first indicated amount of time and the second indicated amount of time comprises a value of thirty seconds or more.

\* \* \* \* \*